United States Patent [19]
Lajoie et al.

[11] Patent Number: 5,552,084
[45] Date of Patent: Sep. 3, 1996

[54] FREE-FLOWING POTASSIUM BICARBONATE COMPOSITION

[75] Inventors: M. Stephen Lajoie, Basking Ridge; Robin C. Sargent, Willingboro, both of N.J.

[73] Assignee: Church & Dwight Co., Inc., Princeton, N.J.

[21] Appl. No.: 558,411

[22] Filed: Nov. 16, 1995

Related U.S. Application Data

[63] Continuation of Ser. No. 277,605, Jul. 20, 1994, abandoned.

[51] Int. Cl.$^6$ .................................................. C01D 7/42
[52] U.S. Cl. ..................... 252/385; 423/419.1; 423/421; 423/920.2
[58] Field of Search ..................... 252/385, 7, 174.13; 423/419.1, 420.2, 421

[56] References Cited

U.S. PATENT DOCUMENTS

| | | | |
|---|---|---|---|
| 639,674 | 12/1899 | Edwards | 252/385 |
| 3,267,030 | 8/1966 | Dessart | 252/7 |
| 5,422,087 | 6/1995 | Lajoie | 423/267 |
| 5,441,669 | 8/1995 | Seper et al. | 252/385 |

OTHER PUBLICATIONS

Hawley's *Condensed Chemical Dictionary*, 11th edition, 1967, p. 1117.
Grant and Hackh's *Chemical Dictionary*, 4th edition, McGraw–Hill Book Company, New York, 1987; pp. 348–349, 639, 573.
Hawley's *Condensed Chemical Dictionary*, 11th edition, Van Nostrand Reinhold Co., 1987, pp. 1 and 447.

*Primary Examiner*—Sharon Gibson
*Assistant Examiner*—Valerie Fee
*Attorney, Agent, or Firm*—Irving M. Fishman

[57] ABSTRACT

This invention provides a process for producing a particulate potassium bicarbonate composition which maintains its free-flow properties when stored under ambient temperature and relative humidity conditions. In the process, particulate potassium bicarbonate is blended with fine grain alkaline earth metal oxide, and the oxide is microdispersed on the surface of the particles. The oxide reacts with moisture and carbon dioxide to form an adherent physically-bonded coating of alkaline earth metal carbonate on the surface of the potassium bicarbonate particles. The altered particle surface prevents agglomeration of the potassium bicarbonate particles.

3 Claims, No Drawings

5,552,084

FREE-FLOWING POTASSIUM BICARBONATE COMPOSITION

This application is a continuation of application Ser. No. 08/277,605, filed Jul. 20, 1994, now abandoned.

BACKGROUND OF THE INVENTION

It is known that the physicochemical properties of solids in particulate form are influenced by the size and shape of the particles. As particle size of solids diminishes in scale, there is an enhancement of properties, and often the inception of new properties.

New commercial products are becoming available which provide special advantage because of fine particle size. Zinc oxide is widely utilized as an ingredient in human health products. Superior results are now obtained by the use of submicron transparent zinc oxide powder.

Alkali metal bicarbonate is another commodity reagent which has found application in a broad variety of products such as laundry detergents, deodorizers, creams and lotions, dentifrices, antacids, buffers, fungicides, and the like.

There is evidence that fine particle size alkali metal bicarbonate can exhibit increased reactivity in comparison with coarse grain bicarbonate salts. In soda cracker production, finely divided sodium bicarbonate or potassium bicarbonate ingredient is more efficiently distributed and effectively reactive during the cracker dough preparation. The finished baked cracker is an improved product which has a substantially uniform texture, flavor and surface color, and a consistent pH throughout.

The inclusion of particulate alkali metal bicarbonate in an antiperspirant-deodorant cosmetic stick provides a product with improved deodorant properties. However, coarse or agglomerated particles of alkali metal bicarbonate have an undesirable tendency to settle in an antiperspirant-deodorant cosmetic stick matrix. The use of free-flowing ultrafine alkali metal bicarbonate as a deodorant ingredient in cosmetic stick and roll-on type personal care products is being investigated, since the ultrafine particles have less tendency to settle than coarse grain particles when dispersed in a liquid or semi-solid matrix.

A limiting factor has been the unavailability of alkali metal bicarbonate powder which is composed of free-flowing ultrafine particles that are not in an agglomerated state. Under ambient conditions of temperature and relative humidity, fine grain potassium bicarbonate powder undergoes caking in a short period of time and gradually converts into a hard mass.

The technical literature reports various means which have been developed for controlling the caking tendency in specific types of bulk inorganic powders.

U.S. Pat. No. 1,150,901 describes a means of stabilizing sodium bicarbonate powder by treating the powder with a saturated aqueous solution of di-sodium phosphate, and removing the water to provide sodium bicarbonate which is admixed with about 3% di-sodium phosphate as a stabilizing agent.

U.S. Pat. No. 1,869,235 describes a method of stabilizing hygroscopic ammonium bicarbonate powder by treating the powder with aqueous sodium chloride to cause a conversion of the ammonium bicarbonate on the particle surfaces to sodium bicarbonate and ammonium chloride, which form a protective coating on the particle surfaces.

U.S. Pat. No. 1,869,518 describes the production of free-flowing alkali metal iodide powder by admixing the powder with about 2% of an alkaline earth metal oxide. The metal oxide additive functions as a moisture scavenger and prevents the hygroscopic alkali metal iodide from absorbing water and suffering loss of free-flow properties.

U.S. Pat. No. 1,894,149 describes a process for stabilizing particulate ammonium bicarbonate which involves contacting the ammonium bicarbonate with ammonium chloride vapor to form a protective coating on the bicarbonate particles.

U.S. Pat. No. 1,907,076 describes a process for preparing an inorganic salt such as hygroscopic calcium chloride in a free-flowing form, which involves admixing the inorganic salt with an alkaline earth metal oxide additive such as magnesium oxide or calcium oxide. The oxide additive chemically combines with the calcium chloride water of crystallization to form a protective coating of alkaline earth metal hydroxide on the surface of the calcium chloride particles.

U.S. Pat. No. 2,218,031 describes a method for maintaining particulate sodium perborate tetrahydrate ($NaBO_3 \cdot 4 H_2O$) is a free-flowing state, which involves admixing the perborate with a small amount of magnesium oxide that has a low bulk density. It was found that magnesium hydroxide was ineffective as a free-flow aid in bulk sodium perborate tetrahydrate.

There is continuing interest in the development of methods for providing inorganic powders which remain in a free-flowing state, particularly when the powders normally are susceptible to agglomeration under ambient conditions of temperature and relative humidity.

Accordingly, it is an object of this invention to provide a process for preparing particulate potassium bicarbonate in a form which maintains its free-flowing properties when stored under ambient conditions of temperature and relative humidity.

It is another object of this invention to provide a free-flowing particulate potassium bicarbonate composition which has a protective coating physically-bonded on the surface of the potassium bicarbonate particles.

Other objects and advantages of the present invention shall become apparent from the accompanying description and examples.

DESCRIPTION OF THE INVENTION

One or more objects of the present invention are accomplished by the provision of a process for producing a free-flowing potassium bicarbonate composition which comprises (1) preparing free-flowing crystalline potassium bicarbonate which has an average particle size between about 10–1000 microns, and has a content of between about 0.01–0.5 weight percent of a microdispersion of potassium carbonate crystallites coated on the surface of the potassium bicarbonate particles; (2) blending the particulate potassium bicarbonate with between about 0.1–1 weight percent of alkaline earth metal oxide which has an average particle size between about 1–200 microns; and (3) recovering a free-flowing potassium bicarbonate composition which accumulates less than about 3.5 weight percent of potassium bicarbonate particles in agglomerated form, after exposure to 80° F. and 80 percent relative humidity conditions for three months.

In another embodiment this invention provides a free-flowing crystalline potassium bicarbonate composition which has an average particle size between about 10–1000 microns, and has a content of between about 0.2–2 weight percent of alkaline earth metal carbonate which is distributed as an adherent physically-bonded coating on the surface of the potassium bicarbonate particles. A carbonate salt such as potassium carbonate can be in the crystalline form of one or more of $K_2CO_3$, $K_2CO_3.1.5\ H_2O$ and $K_2CO_3.2\ KHCO_3.1.5\ H_2O$ chemical structures on the surface of the potassium bicarbonate particles.

The term "physically-bonded" as employed herein refers to an adherent alkaline earth metal carbonate coating which is formed by chemical reaction on the surface of potassium bicarbonate particles. It is believed that the coating is structurally integrated by bonding of divalent alkaline earth metal cations between particle surface bicarbonate anions and coating carbonate anions.

Potassium bicarbonate is a specialty chemical which is produced in industrial-scale quantities by processes such as the carbonation of potassium carbonate in a continuous aqueous slurry operation as illustrated in Example I.

Potassium bicarbonate produced by a carbonation processes typically has a content of less than about one weight percent of potassium carbonate which is distributed in the form of crystallites on the surface of the potassium bicarbonate particles.

Additionally, under ambient conditions of relative humidity at or above the hygroscopicity threshold, the particle surface molecules of potassium bicarbonate gradually convert into potassium carbonate, carbon dioxide and water. This is the reverse of the original potassium carbonate carbonation reaction. As illustrated in Example II, the potassium carbonate crystallites on the potassium bicarbonate particle surface are hygroscopic, and crystalline bridges between adjacent potassium bicarbonate particles form readily, and the result is particle agglomeration and caking within the bulk potassium bicarbonate, and the loss of free-flow properties. Agglomerated potassium bicarbonate is not acceptable for applications which require a free-flowing fine grain product such as in baked goods manufacture.

The present invention process provides a particulate potassium bicarbonate composition which maintains its free-flowing properties for a period of three months or longer under ambient conditions of temperature and relative humidity.

In the practice of a present invention process embodiment, bulk potassium bicarbonate is blended with fine grain alkaline earth metal oxide additive. Suitable alkaline earth metal oxides include magnesium oxide, calcium oxide, zinc oxide, and the like, and any mixture thereof.

The alkaline earth metal oxide microcrystallites are distributed as a dispersion on the surface of the potassium bicarbonate particles. The alkaline earth metal oxide dispersion is in contact with the internalsmoisture content of the potassium bicarbonate substrate, and with the potassium carbonate crystallites residing on the potassium bicarbonate particle surface. The alkaline earth metal oxide dispersion also is in contact with atmospheric moisture and carbon dioxide.

The potassium bicarbonate particle surface conditions are favorable for chemical reaction of the alkaline earth metal oxide with the proximate reactive species. In one reaction the alkaline earth metal oxide interacts with atmospheric moisture and carbon dioxide to form alkaline earth metal carbonate.

In another reaction the external coating alkaline earth metal carbonate molecules can interact with the potassium bicarbonate molecules within the particle surface, and the divalent alkaline earth metal cations can form bridging bonds between the particle internal bicarbonate anions and the external coating carbonate anions.

The resultant potassium bicarbonate particles have an altered surface topography which inhibits the formation of crystalline bridges between adjacent potassium bicarbonate particles, and promotes the preservation of excellent free-flow properties under normal storage conditions.

An essential aspect of the present invention is the in situ formation of alkaline earth metal carbonate on the potassium bicarbonate particle surface, and the consequential adherent bonding of the alkaline earth metal carbonate coating to the underlying particle surface. In contradistinction, as illustrated in Example IV the incorporation of particulate magnesium carbonate additive in bulk potassium bicarbonate does not prevent particle agglomeration and loss of free-flow properties.

The following examples are further illustrative of the present invention. The components and specific ingredients are presented as being typical, and various modifications can be derived in view of the foregoing disclosure within the scope of the invention.

EXAMPLE I

This Example illustrates a process for producing potassium bicarbonate by carbonation of potassium carbonate.

The process involves the reaction of potassium carbonate with carbon dioxide and water to form potassium bicarbonate:

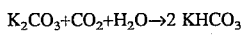

$$K_2CO_3+CO_2+H_2O\rightarrow 2\ KHCO_3$$

The process is operated in the form of a continuous slurry. The reaction rate is controlled by the absorption-rate of carbon dioxide in the aqueous reaction medium. The potassium carbonate and water are metered as separate feed streams into the aqueous reaction medium.

The pH of the aqueous medium is maintained below about 11.8, and the temperature is controlled in the range of 110°–140° F. by heat-exchange of the exothermic heat of reaction. The potassium carbonate is dissolved in the aqueous medium, and the potassium bicarbonate crystallizes out of solution as it forms.

Slurry density is controlled by adjusting the rate of product stream flow out of the reactor unit, and through a draw pump to a hydroclone and centrifuge. The hydroclone and centrifuge operate in series to dewater the potassium bicarbonate crystals to about 4 weight percent. The separated aqueous liquid is recycled to the reactor unit.

The dry potassium bicarbonate product is delumped, and optionally is screened to provide various particle size classifications. The particle size distribution of a typical potassium bicarbonate product of the above described process is as follows:

| Screen Mesh Size | Retained Weight % |
|---|---|
| 20 (840 microns) | less than 1 |
| 40 | less than 5 |
| 60 | 15–45 |
| 80 | 20–35 |
| 100 | 10–25 |
| 200 | 10–30 |
| 325 (44 microns) | less than 10 |
| remainder | less than 5 |

Potassium bicarbonate adapted for utility in the baking industry nominally has an average particle size between about 150–200 microns.

EXAMPLE II

This Example illustrates the flow properties of particulate potassium bicarbonate which is produced by carbonation of potassium carbonate in an aqueous slurry type process.

A commercially-packaged paper bag of potassium bicarbonate (50 pounds, particle size distribution between about 44–840 microns) is opened, and stored in a ventilated chamber for two weeks at 70° F. and 50% relative humidity. After the two week period, the bulk potassium bicarbonate contains a small amount of small lumps and is free-flowing. Analysis of the potassium bicarbonate indicates that it has a 0.05% content of potassium carbonate.

A second bag of potassium bicarbonate is opened, and stored for two weeks at 80° F. and 80% relative humidity. After the two week period, the bulk potassium bicarbonate is wet and non-flowing. Analysis of the potassium bicarbonate indicates that it has a 0.34% content of potassium carbonate.

The potassium carbonate content is formed by the decomposition of potassium bicarbonate in the presence of water:

$$2\ KHCO_3 \rightarrow K_2CO_3 + H_2O + CO_2$$

The potassium carbonate is present as crystallites on the surface of the potassium bicarbonate particles. The potassium carbonate is hygroscopic, and causes particle agglomeration and caking in the bulk potassium bicarbonate, and the loss of free-flow properties. In practice, the caking problem occurs when commercial grade potassium bicarbonate is packaged in non-barrier paper bags under ambient temperature and relative humidity storage conditions.

EXAMPLE III

This Example illustrates the effectiveness of magnesium oxide as a free-flow aid in potassium bicarbonate powder.

A series of tests are conducted to determine the ability of magnesium oxide and three types of silica gels to inhibit particle agglomeration and lumping in a commercial type bulk potassium bicarbonate.

The test procedure involves the following steps:

(1) the crystalline potassium bicarbonate powder is passed through an 840 micron screen;

(2) 0.75% of flow aid is added to 1600 grams of potassium bicarbonate in a quart jar and thoroughly mixed for 15 minutes;

(3) 200 grams of a potassium bicarbonate/flow aid mixture is weighted into a one-half pound newsback box (Arm & Hammer yellow type), and the box is placed in an 80° F./80% relative humidity oven for a testing period; a corresponding box is placed in desiccator at 70° F./50% relative humidity as a control;

(4) at the end of a designated test period, the box contents are emptied onto a 3360 micron rotap screen, and all the potassium bicarbonate which does not pass through the screen is recorded as soft lump weight;

(5) the soft lump weight is transferred to a 840 micron (20 mesh) rotap screen, and the screen is shaken for 10 seconds; lumps which remain on the screen are recorded as hard lump weight; and (6) the test results are compared in terms of weight percent SOFT LUMPS/HARD LUMPS for the 80° F./80% relative humidity samples, as summarized in Table I.

TABLE I

|  | 90 days |
|---|---|
| Sylox 15[1] | 95.9/23.2 |
| Flow-Gard SP[2] | 99.1/37.6 |
| Flow-Gard AB[3] | 93.2/15.6 |
| MgO[4] | 0/0.04 |

[1]Synthetic amorphous silica (Davison Chemical).
[2]Silica gel (PPG Industries).
[3]Silica gel (PPG Industries).
[4]Light density; 99% through 325 mesh (Whittaker, Clark & Daniels).

There is no evidence of lumping in the control samples which are stored in the desiccator at 70° F./50% relative humidity for 90 days.

The comparative data in Table I demonstrate that magnesium oxide is a superior free-flow aid for potassium bicarbonates in comparison to the three types of silica compounds tested.

EXAMPLE IV

This Example illustrates the superior properties of the present invention alkaline earth metal oxides as free-flow aids for potassium bicarbonate in comparison with a commercial free-flow aid product.

A.

The comparative test procedures described in Example III are employed. The test results are compared in terms of weight percent SOFT LUMPS/HARD LUMPS for the 80° F./80% relative humidity samples, as summarized in Table II.

TABLE II

|  | 7 days | 30 days | 60 days | 90 days |
|---|---|---|---|---|
| 0.25% MgO | 2/0 | 18.75/0 | 43.9/0 | 48.2/2.5 |
| 0.5% MgO | 2/0 | 22.65/0 | 42.2/0 | 45.0/3.2 |
| 0.75% TCP[1] | 3/0 | 0/0 | 40.2/0 | 38.5/0 |

[1]Tricalcium phosphate (Monsanto).

The control samples stored in the desiccator at 70° F./50% relative humidity are lump-free after 90 days.

A combination of 80° F. temperature and 80° F. relative humidity causes lumping and caking in potassium bicarbonate powder control samples.

The comparative data demonstrate that after three months at 80° F./80% relative humidity, the potassium bicarbonate samples containing magnesium oxide exhibit good free-flow properties, while the samples containing tricalcium phosphate exhibit poor free-flow properties.

Similar results are observed when calcium oxide and zinc oxide, respectively, are employed as a flow aid instead of magnesium oxide.

Analytical methods indicate that the magnesium oxide initially on the surface of the treated potassium bicarbonate particles has chemically transformed into a magnesium carbonate protective coating. The protective coating appears to have a bridging type of chemical bonding which structurally integrates the coating with the particle surface.

Using yellow box stability test procedures, particulate magnesium carbonate and tricalcium phosphate are inferior to magnesium oxide for purposes of inhibiting particle agglomeration and caking in potassium bicarbonate powder samples, as summarized in Table III.

TABLE III

|  | MgCO$_3$ (0.75%) | TCP (0.75%) |
| --- | --- | --- |
| (a) one month | | |
| Control 70° F./50% relative humidity Samples | free flowing 0% soft lumps 0% hard lumps poor flow | free flowing 0% soft lumps 0% hard lumps poor flow |
| 80° F./80% relative humidity | 48% soft lumps 9.5% hard lumps | 24% soft lumps 4.5% hard lumps |
| (b) two months | | |
| Control 70° F./50% | free flowing 0% soft lumps 0% hard lumps | free flowing 0% soft lumps 0% hard lumps |
| Samples 80° F./80% | poor flow 81% soft lumps 48% hard lumps | poor flow 91% soft lumps 67% hard lumps |

Under comparative testing conditions, potassium bicarbonate samples with 0.75% magnesium oxide additive remain free-flowing.

What is claimed is:

1. A free-flowing crystalline potassium bicarbonate composition which has an average particle size between about 10–1000 microns, and has a content of between about 0.2–2 weight percent of magnesium carbonate which is distributed as an adherent physically-bonded coating on the surface of the potassium bicarbonate particles; wherein the composition accumulates less than about 3.5 weight percent of potassium bicarbonate particles in agglomerated form, after exposure to 80° F. and 80 percent relative humidity conditions for three months.

2. A process for producing a free-flowing potassium bicarbonate composition which comprises (1) preparing free-flowing crystalline potassium bicarbonate which has an average particle size between about 10–1000 microns, and has a content of between about 0.01–0.5 weight percent of a microdispersion of potassium carbonate crystallites coated on the surface of the potassium bicarbonate particles; (2) blending the particulate potassium bicarbonate with between about 0.1–1 weight percent of magnesium oxide which has an average particle size between about 1–200 microns; and (3) recovering a free-flowing potassium bicarbonate composition which accumulates less than about 3.5 weight percent of potassium bicarbonate particles in agglomerated form, after exposure to 80° F. and 80 percent relative humidity conditions for three months.

3. A process in accordance with claim 2 wherein the average particle size of the potassium carbonate microdispersion crystallites in step(1) is between about 0.05–2 microns.

* * * * *